(12) United States Patent
Daly et al.

(10) Patent No.: US 6,426,436 B1
(45) Date of Patent: Jul. 30, 2002

(54) ETHER DIAMINES QUATERNARIES

(75) Inventors: Thomas J. Daly, Barrington, IL (US); Michael Clumpner, Delevan, WI (US); Anthony J. O'Lenick, Jr., Dacula, GA (US)

(73) Assignee: Nova Molecular Technologies Inc., Jamesville, WI (US)

( * ) Notice: Subject to any disclaimer, the term of this patent is extended or adjusted under 35 U.S.C. 154(b) by 0 days.

(21) Appl. No.: 10/051,675

(22) Filed: Jan. 22, 2002

Related U.S. Application Data

(60) Division of application No. 09/722,197, filed on Nov. 27, 2000, which is a continuation-in-part of application No. 09/566,505, filed on May 8, 2000, now Pat. No. 6,331,648, which is a continuation-in-part of application No. 09/459,562, filed on Dec. 13, 1999, now Pat. No. 6,114,585.

(51) Int. Cl.[7] .................. C07C 211/63; C07C 211/64
(52) U.S. Cl. .................. 564/286; 564/293; 564/294; 564/295
(58) Field of Search ................... 564/286, 293, 564/294, 295

(56) References Cited

U.S. PATENT DOCUMENTS

| 4,579,560 A | * | 4/1986 | Cargnino et al. | .............. 8/539 |
| 5,070,202 A |   | 12/1991 | Herkes |  |

* cited by examiner

*Primary Examiner*—Brian J. Davis

(57) ABSTRACT

The present invention is related to a series of derivatives of novel ether diamine compounds prepared by the cynobutylation reaction of an alcohol having 3 to 22 carbon atoms with 2-pentenenitrile to form a branched alkyl ether nitrile. The etheraminonitriles formed by the process are hydrogenated to form alkylether amines. The resulting product can be reacted with 2-pentenenitrile and or acrylonitrile and in subsequent step, hydrogenated to yield a diamine. Specifically, the present invention deals with two types of tertiary amines one made by the reaction of novel ether diamines compounds with ethylene oxide, propylene oxide or butylene oxide or mixtures thereof, producing alkoxylated tertiary amines and the other made by the reaction of novel ether amine compounds with formaldehyde and hydrogen producing methylated tertiary amines. The invention also disclosed novel amine oxides, and quaternary compounds made from said tertiary amines.

2 Claims, No Drawings

ETHER DIAMINES QUATERNARIES

RELATED APPLICATION

This application is a divisional application of Ser. No. 09/722,197 filed Nov. 27, 2000, which in turn is a continuation in part of application Ser. No. 09/459,562 filed Dec. 13, 1999, now U.S. Pat. No. 6,114,585 issued September 2000, which is a continuation in part of application Ser. No. 09/566,505 filed May 8, 2000, now U.S. Pat. No. 6,331,648 issued December 2001.

FIELD OF THE INVENTION

The present invention relates to a series of derivatives of novel ether diamine compounds prepared by the cyanobutylation reaction of an alcohol having 3 to 22 carbon atoms with 2-pentenenitrile to form a branched alkyl ether nitrile. The alkyl ether nitriles formed by the process are hydrogenated to form alkylether amines. The resulting products are then reacted with 2-pentenenitrile or acrylonitrile and hydrogenated to yield a diamine, which can likewise be derivatized. Specifically, the present invention deals with two types of tertiary amines, one made by the reaction of novel ether diamines compounds with ethylene oxide, propylene oxide, butylene oxide or mixtures thereof producing alkoxylated tertiary diamines and the other conveniently made by the reaction of novel ether diamine compounds with formaldehyde and hydrogen producing methylated tertiary diamines. The invention also discloses novel diamine oxides, and quaternary compounds made from said tertiary amines.

BACKGROUND OF THE INVENTION

U.S. Pat. Nos. 4,260,556 and 4,211,725 teach reaction of 2-pentenenitrile with ammonia or ethylenediamine to produce alkylaminonitriles. U.S. Pat. No. 4,496,474 teaches the reaction of 2-pentenenitrile with alkylamines having from 8 to 22 carbons to produce the corresponding nitrile compound. U.S. Pat. No. 5,070,202 teaches a process having improved reaction rate and selectivity in the reaction of 2-pentenenitrile with amines to form alkylaminonitriles by the incorporation of from 15 to 60 weight percent water in the reaction mixture. These references do not include the critical ether linkage needed to make the products of the present invention.

U.S. Pat. No. 5,902,883 to Herkes discloses the cyanobutylation of various amines to make diamines. Herkes uses 3-pentenenitrile, 4-pentenenitrile or mixtures of 3-pentenenitrile and 4-pentenenitrile to make his product. This does not result in the desired branching that comes from the compounds of the present invention, nor does it include the critical ether linkage in the molecule. Herkes has done some work with the cyanobutylation of lower molecular weight alcohols (C3 to C8) to form primary amines. These materials lack the hydrophobicity to be good surface-active agents.

It has now been found that by reacting alcohols with 2-pentenenitrile and hydrogenating to the alkyloxypentyl amines, followed by cyonoethylation or cyonobutylation to form diamines, followed by alkoxylation or methylation to form tertiary amines and in a subsequent step derivitization of said tertiary amines results in products with unique properties. Further reaction to form the salts, quaternary salts, or amine oxides also result in products with unique properties. These include (a) superior liquidity of the resulting products, (b) improved surfactant properties and (c) improved solubility. All of these will become clear as one reads the teachings of the present invention.

SUMMARY OF THE INVENTION

The present invention relates to a series of derivatives of novel ether diamine compounds prepared by the cyanobutylation reaction of an alcohol having 3 to 22 carbon atoms with 2-pentenenitrile to form a branched alkyl ether nitrile. The alkyl ether nitrites formed by the process are hydrogenated to form alkylether amines. The ether amine compounds may be used as raw materials for the preparation of the derivatives of the current invention which are the topic of application Ser. No. 459,562 filed Dec. 13, 1999, now U.S. Pat. No. 6,114,585 issued September 2000, and application Ser. No. 09/566,505 filed May 8, 2000 incorporated herein by reference. The resulting product can be reacted with 2-pentenenitrile and or acrylonitrile and in a subsequent step, hydrogenated, to yield a diamine. Specifically, the present invention deals with two types of tertiary amines. One made by the reaction of novel ether diamine compounds with ethylene oxide, propylene oxide, butylene oxide or mixtures thereof to produce an alkoxylated tertiary diamine, and the other conveniently made by the reaction of novel ether diamine compounds with formaldehyde and hydrogen to produce a methylated tertiary diamine. The invention also discloses novel amine oxides, amine salts and quaternary compounds made from said tertiary diamines.

DETAILED DESCRIPTION OF THE INVENTION

The present invention relates to a series of derivatives of novel ether diamine compounds prepared by the cyanobutylation reaction of an alcohol having 3 to 22 carbon atoms with 2-pentenenitrile to form a branched alkyl ether nitrile. The etheraminonitriles formed by the process are hydrogenated to form alkyl ether amines. The resulting product can be reacted with 2-pentenenitrile or acrylonitrile and hydrogenated to yield a diamine. Specifically, the present invention deals with two types of tertiary amines, one made by the reaction of novel ether diamine compounds with ethylene oxide, propylene oxide or butylene oxide or mixtures thereof producing alkoxylated tertiary diamines and the other made by the reaction of novel ether diamine compounds with formaldehyde and hydrogen producing methylated tertiary diamines. The tertiary ether diamines are also converted to amine oxides and quaternaries.

The compounds of the present invention are diamines and derivatives falling into the following classes:

Class 1

A branched ether diamine conforming to the following structure:

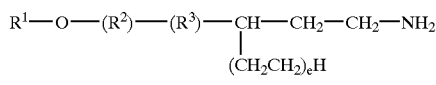

wherein;

e is 0 or 1;

$R^1$ is selected from the group consisting of alkyl having 3 to 22 carbon atoms;

$R^2$ is $-(CH_2CH_2O)_a-(CH_2CH(CH_3)O)_b-(CH_2CH(CH_2CH_3)O)_c-$;

a, b and c are independently integers ranging from 0 to 30;

$R^3$ is

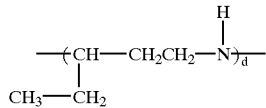

d is 1.

Class 2

An alkoxylated tertiary ether diamine conforming to the following structure:

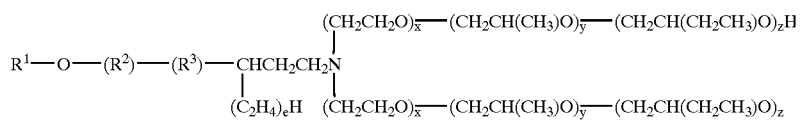

wherein;

$R^1$ is selected from the group consisting of alkyl having 3 to 22 carbon atoms, aryl having 6 to 20 carbon atoms;

$R^2$ is $-(CH_2CH_2O)_a(CH_2CH(CH_3)O)_b-(CH_2CH(CH_2CH_3)O)_c-$;

a, b and c are independent integers ranging from 0 to 30, with the provision that a+b+c are a minimum of 0 and a maximum of 60;

$R^3$ is

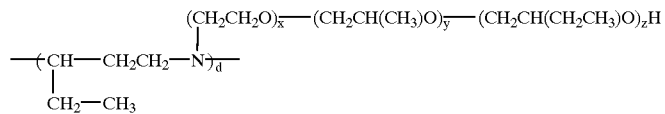

d is 1;

e is 0 or 1;

x, y and z are integers ranging from 0 to 30 with the provision that x+y+z is a minimum of 2 and a maximum of 60.

Class 3

An alkoxylated tertiary ether diamine oxide conforming to the following structure:

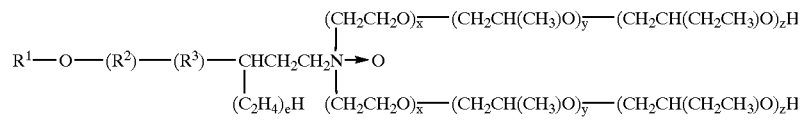

wherein;

$R^1$ is selected from the group consisting of alkyl having 3 to 22 carbon atoms, aryl having 6 to 20 carbon atoms;

$R^3$ is

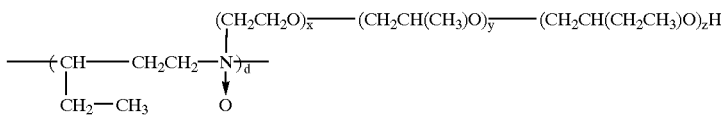

d is 1;

e is 0 or 1;

x, y and z are integers ranging from 0 to 30 with the provision that x+y+z is a minimum of 2 and a maximum of 60.

Class 4

A trimethyl tertiary ether diamine conforming to the following structure:

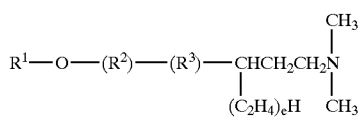

wherein;

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-(CH_2CH(CH_2CH_3)O)_c-$;

a, b and c are independent integers ranging from 0 to 30, with the provision that a+b+c are a minimum of 0 and a maximum of 60;

$R^3$ is

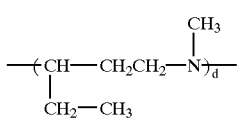

d is 1;

e is 0 or 1.

Class 5

A trimethyl tertiary ether diamine oxide conforming to the following structure:

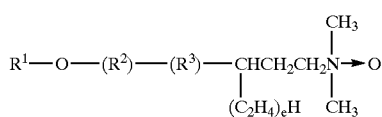

wherein:

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-(CH_2CH(CH_2CH_3)O)_c-$;

a, b and c are independent integers ranging from 0 to 30, with the provision that a+b+c are a minimum of 0 and a maximum of 60;

$R^3$ is

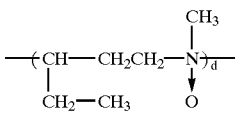

d is 1;

e is 0 or 1.

Class 6

An ether diamine quaternary conforming to the following structure:

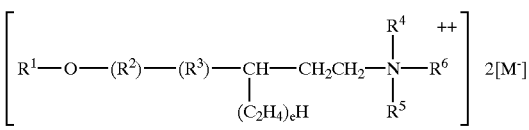

wherein:

$R^1$ is selected from the group consisting of alkyl having 3 to 22 carbon atoms;

$R^2$ is $-(CH_2CH_2O)_a-(CH_2CH(CH_3)O)_b-(CH_2CHCH_2CH_3)O)_c-$;

a, b and c are independent integers ranging from 0 to 30;

$R^3$ is

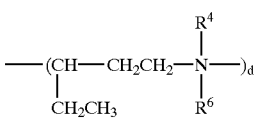

d is 1;

e is 0 or 1;

$R^4$ and $R^5$ are selected from the group consisting of $-CH_3$ and $-(CH_2CH_2O)_x-(CH_2CH(CH_3)O)_y-(CH_2CH(CH_2CH_3)O)_zH$;

x, y and z are independent integers ranging from 0 to 20, with the provision that x+y+z is greater than or equal to 3;

$R^6$ is selected from the group consisting of $-CH_3$ and $-CH_2-C_6H_5$

M is an appropriate anion needed for charge balance such as Cl, Br, and $CH_3SO_4$, etc.

Each of the various classes of compounds has in common the fact that they are derivatives of a penetene nitrile diamine. The preparation of the compounds of the present invention includes the following steps: (1) reaction of an ether amine with pentene nitrile or acrylonitrile followed by (2) hydrogenation of the nitrile to the diamine, followed by (3) reaction with either formaldehyde and hydrogen or alkoxylated to form a tertiary ether diamine then (4) derivatization of the tertiary amine into an amine oxide or quaternary compound.

Preferred Embodiments

In a preferred embodiment of the branched ether diamine conforming to the following structure:

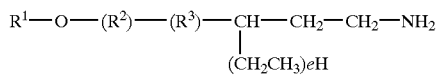

wherein;

e is 0 or 1;

$R^1$ is selected from the group consisting of alkyl having 3 to 22 carbon atoms;

$R^2$ is $-(CH_2CH_2O)_a-(CH_2CH(CH_3)O)_b-(CH_2CH(CH_2CH_3)O)_c-$;

a, b and c are independently integers ranging from 0 to 30;

$R^3$ is

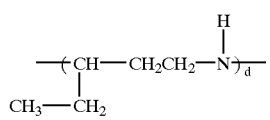

d is 1;

$R^1$ is $C_{12}H_{25}$, a, b and c are each 0, d is 1 and e is 1.

In another preferred embodiment of the branched ether diamine $R^1$ is hydrogenated tallow, a, b and c are each 0, and e is 0.

In still another preferred embodiment of the ether diamine $R^1$ is $C_{12}H_{25}$, a, b and c are each 0, and e is 0.

In a preferred embodiment of the branched ether diamine, $R^1$ is hydrogenated tallow, a, b and c are each 0, and e is 0.

In a preferred embodiment of the alkoxylated tertiary ether diamine conforming to the following structure:

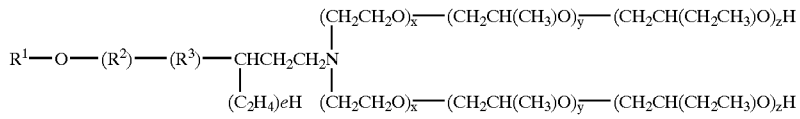

wherein;

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-(CH_2CH(CH_2CH_3)O)_c-$;

a, b and c are independent integers ranging from 0 to 30, with the provision that a+b+c are a minimum of 0 and a maximum of 60;

$R^3$ is

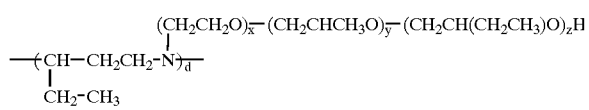

d is 1;

e is 0 or 1;

x, y and z are integers ranging from 0 to 30 with the provision that x+y+z is a minimum of 2 and a maximum of 60; $R^1$ is $C_{12}H_{25}$, a, b, and c each 0, x is 5, and e is 1.

In another preferred embodiment of the alkoxylated tertiary ether diamine $R^1$ is $C_{13}H_{27}$, a is 0, b is 0, c is 30, y is 2, d is 1 and e is 1.

In another preferred embodiment of the alkoxylated tertiary ether diamine $R^1$ is $C_{12}H_{25}$, a, b, and c each 0, x is 5, and e is 0.

In still another preferred embodiment of the alkoxylated tertiary ether diamine $R^1$ is $C_{13}H_{27}$, a is 0, b is 0, c is 30, y is 2, and e is 0.

A preferred embodiment of the alkoxylated tertiary ether diamine oxide conforming to the following structure:

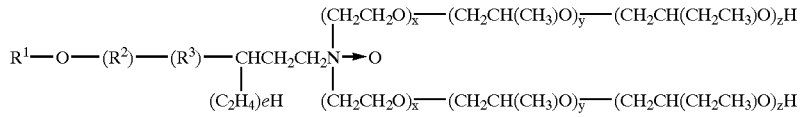

wherein;

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-(CH_2CH(CH_2CH_3)O)_c-$;

a, b and c are independent integers ranging from 0 to 30, with the provision that a+b+c are a minimum of 0 and a maximum of 60;

R³ is $$-(CH-CH_2CH_2-N)_d-$$
$$\phantom{-(}|\phantom{CH_2CH_2-N}\downarrow$$
$$\phantom{-(}CH_2-CH_3\phantom{CH_2-N}O$$

with $(CH_2CH_2O)_{\overline{x}}(CH_2CH(CH_3)O)_{\overline{y}}(CH_2CH(CH_2CH_3)O)_zH$ branch on N.

d is 1;

e is 0 or 1;

x, y and z are integers ranging from 0 to 30 with the provision that x+y+z is a minimum of 2 and a maximum of 60 is when $R^1$ is $C_{10}H_{21}$, a, b and c are each 0, x is 60, and e is 1.

In another preferred embodiment of the alkoxylated tertiary diamine oxide $R^1$ is $C_8H_{17}$, a is 1, b is 30, c is 2, x is 1 and y is 2, and e is 1.

In another preferred embodiment of the alkoxylated tertiary diamine oxide $R^1$ is $C_{10}H_{21}$, a, b and c are each 0, x is 60, and e is 0.

In still another preferred embodiment of the alkoxylated tertiary diamine oxide of $R^1$ is $C_8H_{17}$, a is 1, b is 30, c is 2, x is 1 and y is 2, and e is 0.

In a preferred embodiment of the trimethyl tertiary ether diamine conforming to the following structure:

$$R^1-O-(R^2)-(R^3)-CHCH_2CH_2N\begin{array}{c}CH_3\\|\\|\\(CH_2CH_2)eH\phantom{x}CH_3\end{array}$$

wherein;

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-CH_2CH(CH_2CH_3)O)_c-$;

a, b and c are independent integers ranging from 0 to 30, with the provision that a+b+c are a minimum of 0 and a maximum of 60;

$R^3$ is $$-(CH-CH_2CH_2-N)_d-$$
$$\phantom{-(}|\phantom{CH_2CH_2-N}|$$
$$\phantom{-(}CH_2.CH_3\phantom{CH_2-N}O$$

with CH₃ on N.

d is 1;

e is 0 or 1 is when $R^1$ is $C_3H_7$, b is 5, and e is 1.

In another preferred embodiment of the trimethyl tertiary ether diamine $R^1$ is $C_{12}H_{25}$, a is 30, and e is 1.

In another preferred embodiment of the trimethyl tertiary ether diamine $R^1$ is $C_3H_7$, b is 5, and e is 1.

In another preferred embodiment of the trimethyl tertiary ether diamine $R^1$ is $C_{12}H_{25}$, a is 30, and e is 1.

A preferred embodiment of the trimethyl tertiary ether diamine oxide conforming to the following structure:

$$R^1-O-(R^2)-(R^3)-CHCH_2CH_2N\rightarrow O$$
with CH₃ and $(C_2H_4)eH$ groups on N.

wherein:

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-CH_2CH(CH_2CH_3)O)_c-$;

a, b and c are independent integers ranging from 0 to 30, with the provision that a+b+c are a minimum of 0 and a maximum of 60;

$R^3$ is $$-(CH-CH_2CH_2-N)_d-$$
$$\phantom{-(}|\phantom{CH_2CH_2-N}\downarrow$$
$$\phantom{-(}CH_2.CH_3\phantom{CH_2-N}O$$

with CH₃ on N.

d is 1;

e is 0 or 1 is when $R^1$ is $C_8H_{17}$, a is 1, b is 30, c is 2, and e is 1.

Another preferred embodiment of the trimethyl tertiary ether diamine is when $R^1$ is $C_{10}H_{21}$, a, b and c are each 0, and e is 0.

In a preferred embodiment of ether diamine quaternary conforming to the following structure:

$$\left[R^1-O-(R^2)-(R^3)-CH-CH_2CH_2-\overset{R^4}{\underset{R^5}{\overset{|}{\underset{|}{N}}}}-R^6\right]^{++} 2[M^-]$$

with $(C_2H_4)eH$ group.

wherein:

$R^1$ is selected from the group consisting of alkyl having 3 to 22 carbon atoms;

$R^2$ is $-(CH_2CH_2O)_a-(CH_2CH(CH_3)O)_b-(CH_2CHCH_2CH_3)O)_c-$;

a, b and c are independent integers ranging from 0 to 30;

$R^3$ is $$-(CH-CH_2CH_2-\overset{R^4}{\underset{R^6}{\overset{|}{\underset{|}{N}}}}-)_d$$
$$\phantom{-(}|$$
$$\phantom{-(}CH_2CH_3$$

d is 1;

e is 0 or 1;

$R^4$ and $R^5$ are selected from the group consisting of $-CH_3$; and $-(CH_2CH_2O)_x-(CH_2CH(CH_3)O)_y-(CH_2CH(CH_2CH_3)O)_zH$;

x, y and z are independent integers ranging from 0 to 20, with the provision that x+y+z is greater than or equal to 3;

$R^6$ is selected from the group consisting of $-CH_3$ and $-CH_2-C_6H_5$;

M is an appropriate anion needed for charge balance such as Cl, Br, and $CH_3SO_4$, is when $R^1$ is hydrogenated tallow, a, b and c are each 0, $R^4$ and $R^5$ and $R^6$ are $CH_3$ and M is Cl, and e is 0.

Another preferred embodiment of the ether diamine quaternary $R^1$ is $C_3H_7$, b is 5, $R^4$, $R^5$ and $R^6$ are $CH_3$.

Raw Material Amine Preparation

The ether amine compounds used as raw materials for the preparation of the derivatives of the current invention are the topic of application Ser. No. 459,562 filed Dec. 13, 1999, now U.S. Pat. No. 6,114,585 issued September 2000, and application Ser. No. 09/566,505 filed May 8, 2000 incorporated herein by reference. They conform to the following structure;

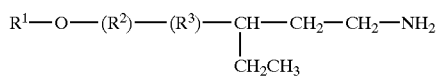

$R^1$ is selected from the group consisting of alkyl having 3 to 22 carbon atoms,
$R^2$ is $—(CH_2CH_2O)_a—(CH_2CH(CH_3)O)_b—(CH_2CH(CH_2CH_3)O)_c—$;
a, b and c are independently integers ranging from 0 to 30,
$R^3$ is

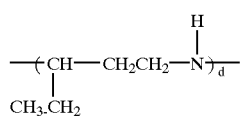

d is 0 or 1.

Class 1: Ether Monoamine (d=0)

The ether monoamines conform to the following structure:

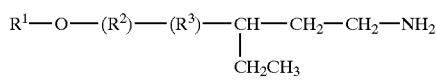

wherein;
$R^1$ is selected from the group consisting of alkyl having 3 to 22 carbon atoms
$R^2$ is $—(CH_2CH_2O)_a—(CH_2CH(CH_3)O)_b—(CH_2CH(CH_2CH_3)O)_c—$;
a, b and c are independently integers ranging from 0 to 30,
$R^3$ is

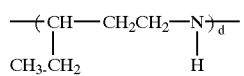

d is 0.

Ether Diamine (d=1)

Ether diamine compounds of the present invention conform to the following structure:

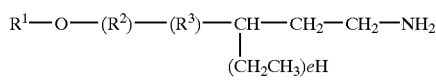

e is 0 or 1;

$R^1$ is selected from the group consisting of alkyl having 3 to 22 carbon atoms
$R^2$ is $—(CH_2CH_2O)_a—(CH_2CH(CH_3)O)_b—(CH_2CH(CH_2CH_3)O)_c—$;
a, b and c are independently integers ranging from 0 to 30,
$R^3$ is

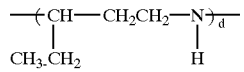

d is 1.

RAW MATERIALS ALCOHOLS

The alcohols and alcohol alkoxylates used in the manufacture of the products of the present invention are well known in the art and are commercially available from a variety of suppliers. Suppliers of these materials include Shell Chemical Company, Condea-Vista, Exxon Chemical Company, Henkel Corporation and Siltech Corporation.

$R^1OR^2—H$

Where $R^2$ is $(CH_2CH_2O)_a—(CH_2CH(CH_3)O)_b—(CH_2CH(CH_2CH_3)O)_c$

| Example | $R^1$ | $R^2$ a | b | c |
|---|---|---|---|---|
| 1 | $C_{12}H_{25}$ | 0 | 0 | 0 |
| 2 | $C_3H_7$ | 0 | 5 | 0 |
| 3 | C8H17 | 0 | 0 | 0 |
| 4 | $C_{10}H_{21}$ | 0 | 0 | 0 |
| 5 | $C_{13}H_{27}$ | 0 | 0 | 0 |
| 6 | Hydrogenated Tallow 40% $C_{16}H_{33}$ & 60% $C_{18}H_{37}$ | 0 | 0 | 0 |
| 7 | Behenyl 30% $C_{20}H_{41}$ & 70% $C_{22}H_{45}$ | 0 | 0 | 0 |
| 8 | $C_{12}H_{25}$ | 30 | 0 | 0 |
| 9 | $C_8H_{17}$ | 1 | 30 | 2 |
| 10 | $C_{13}H_{27}$ | 0 | 0 | 30 |

Procedure

Preparation of Ether Nitrile (Cyanobutylation)

One mole of base alcohol is charged to a reaction flask and one mole plus approximately 10% excess of the 2-pentenenitrile is placed in an addition flask. Material is heated while stirred to a temperature of about 40° C. Base catalyst (KOH) is added based on the total weight of the reactants charged at about a 0.1 to 0.5% or more preferably 0.2–0.3% basis. A nitrogen blanket is applied to the headspace of the reaction vessel and the mixture is stirred for about 15 minutes at 40° C. to incorporate the catalyst into the alcohol. Keep the reaction flask headspace blanketed with nitrogen throughout the entire reaction period.

The addition of the 2-pentenenitrile is exothermic. Charge the 2-pentenentrile to the reaction vessel such that the temperature of reaction is maintained at 40–65° C., more preferably 45–60° C., and most preferably 50–55° C. When all of the 2-pentenenitrile has been added let react for 2 hours at 50° C. After the 2 hours add an equivalent amount of acid to neutralize the base catalyst. Stir mixture for 15 minutes then filter the 3-alkoxy-3-ethylpropylnitrile to be hydrogenated to remove salts formed on neutralization of the KOH.

Hydrogenation of 3-Alkoxy-3 Ethylpropylnitrile

Charge the ether nitrile to an autoclave that is capable of operating at pressures up to 600 psig. Charge 2% by weight of Raney® Nickel (based upon the weight of the alcohol to the vessel). Seal autoclave and start agitation, increase heat to about 80 to 100° C. and vacuum strip out any water that may have been introduced during cyanobutylation or from Raney® nickel. When no more water appears on the condenser of the vacuum set-up, close autoclave and charge hydrogen gas to about 5 psig. Charge ammonia to vessel to about 60 to 70 psig. Increase heat to 135° C. and note pressure. Add hydrogen such that about 150 to 200 psig additional pressure is measured on the autoclave pressure gauge. Maintain continuous hydrogen addition in this manner for a period of 4–6 hours, then close the hydrogen inlet valve and note pressure on the pressure gauge.

Turn off heat and cool to about 70° C. Carefully, open vent to release pressure and vacuum strip to remove ammonia. Discharge the 3-alkoxy-3ethylpropylamine and filter to remove Raney® nickel catalyst.

EXAMPLE 11

Preparation of 3-Dodecyloxy-3-ethylpropylnitrile (Cyanobutylation)

To a 500 ml round bottomed flask fitted with a mechanical stirrer, gas inlet tube and dropping funnel was added 186 g (1 mole) of n-dodecyl alcohol (Example 1) and 0.7 g of KOH. A nitrogen blanket was maintained throughout the procedure. The temperature was increased to 40° C. while stirring to dissolve and disperse the KOH. The dropping funnel was charged with 90.0 g of 2-pentenenitrile (1.11 mole). The nitrile was added with stirring at a rate that kept the reaction temperature from rising over 50° C. After the addition the reaction was allowed to proceed for an additional 2 hours at 50° C. The catalyst, KOH, was then deactivated by neutralization with an equivalent amount of acetic acid. After neutralization the mixture was stirred for 15 minutes and then filtered to remove the salts that formed on neutralization. The excess 2-pentenenitrile was then removed by vacuum stripping.

EXAMPLES 12–20

Example 11 is repeated, only this time replacing the alcohol example with the type and quantity of alcohol shown.

| Ether nitrile Example | Alcohol Example | Grams | KOH (95%) Grams |
|---|---|---|---|
| 12 | 2 | 350.0 | 1.0 |
| 13 | 3 | 130.0 | 0.5 |
| 14 | 4 | 158.0 | 0.5 |
| 15 | 5 | 200.0 | 0.6 |
| 16 | 6 | 259.0 | 0.7 |

-continued

| Ether nitrile Example | Alcohol Example | Grams | KOH (95%) Grams |
|---|---|---|---|
| 17 | 7 | 318.0 | 0.8 |
| 18 | 8 | 1506.0 | 3.8 |
| 19 | 9 | 2054.0 | 5.0 |
| 20 | 10 | 2360.0 | 6.0 |

EXAMPLE 21

Preparation 3-Dodecyloxy-3-ethylpropylamine (Hydrogenation)

Then 265 grams (0.99 mole) of 3-dodecyloxy-3-ethylpropylnitrile was poured into a suitable sized autoclave equipped with stirring. Raney® nickel, 5.3 g was also added. After sealing the autoclave and heating to 80° C. a vacuum was applied while stirring to remove water introduced with the catalyst. When no more water appeared on the condenser of the vacuum set-up the vacuum was released and hydrogen was allowed to fill the vessel to a pressure of 5 psig. Ammonia was then added until the pressure rose to 65 psig. The temperature was then increased to 135° C. that caused the pressure to rise to about 150 psig. The pressure was then increased to 400 psig with hydrogen and the stirring speed increased to 1200 rpm. After 4 hours the valve to the hydrogen cylinder was closed and the pressure in the headspace monitored. Since the pressure dropped by 100 psig over the next 15 minutes, the valve was opened again and the reaction allowed to proceed for another hour. After checking for a pressure drop again, none was noted over the next 15 minutes and the reaction was declared complete. The heat was turned off and cooling water run through the coils until the temperature dropped to 70° C. After venting off the hydrogen and flushing with nitrogen, residual ammonia was vacuum stripped. The product, 3-n-dodecyloxy-3ethylpropylamine, was filtered to remove Raney® nickel catalyst. The yield was essentially quantitive.

Example 21 is repeated, only this time replacing the ether mononitrile of example 12 with the type and quantity shown.

| Ether Mono Amine Example | Ether Nitrile Example | Grams |
|---|---|---|
| 22 | 12 | 435.0 |
| 23 | 13 | 215.0 |
| 24 | 14 | 243.0 |
| 25 | 15 | 285.0 |
| 26 | 16 | 344.0 |
| 27 | 17 | 403.0 |
| 28 | 18 | 1591.0 |
| 29 | 19 | 2139.0 |
| 30 | 20 | 2445.0 |

The products are used to prepare ether diamines and their derivatives that are the subject of this invention.

Class 2: Ether Diamine (d is 1)

Procedure

The products of class 1 are reacted with additional 2-pentenenitrile and or acrylonitrile to make the either aminonitrile, then subsequently reacted with hydrogen to make the ether diamine.

EXAMPLES 31–35 ARE ETHER DIAMINES WHERE D IS 1 AND E IS 1

EXAMPLE 31

Preparation of 3-Dodecyloxy-3-ethylpropylamine Pentenenitrile (Cyanobutylation of Ether Mono Amine)

To a suitable reaction flask is added 275.0 grams of 3-dodecyloxy-3-ethylpropyl amine (example 21). Heat while under agitation to 40° C. A nitrogen blanket is applied to the headspace of the reaction vessel. Keep the reaction flask headspace blanketed with nitrogen throughout the entire reaction period. Begin addition of 90.0 grams of 2-pentenenitrile under good agitation keeping the temperature below 50° C. When all of the 2-pentenenitrile has been added, let react for two hours at 50° C.

Preparation of Diamine (Hydrogenation)

Charge the etheramine pentenenitrile as prepared to an autoclave that is capable of operating at pressures up to 600 psig. Autoclave must be placed in a hood or vented area and must be equipped with vacuum stripping, cooling, and heating. Carefully charge a known quantity of metal catalyst such as Raney Nickel to the vessel. Use 2% by weight based upon the weight of the total batch. Seal autoclave and start agitation, increase heat to about 80 to 100° C. and vacuum strip out any water that may have been introduced during cyanobutylation or from the Raney® Nickel. When no more water appears on the condenser of the vacuum set-up, close autoclave and charge hydrogen gas to about 5 psig. Charge ammonia to vessel up to about 60 to 70 psig. Increase heat to 135° C. and note pressure. Add hydrogen such that about 150 to 200 psig additional pressure is measured on the autoclave pressure gauge. Maintain this increase with hydrogen gas that will be rapidly taken up by the reaction mixture during the first hour of the reaction. Maintain continuous hydrogen addition in this manner for a period of 4 to 6 hours. After this time, close the valve from the hydrogen to the autoclave and note pressure on pressure gauge. If pressure is stable and does not decrease after 15 minutes, reaction is complete. Otherwise, continue adding hydrogen as previously described for one hour and then re-check.

Example 31 is repeated, only this time replacing the ether monoamine of example 31 with the type and quantity of monoether amine shown below:

| Ether Diamine Example | Ether Monoamine Example | Grams |
|---|---|---|
| 32 | 22 | 440.0 |
| 33 | 23 | 220.0 |
| 34 | 24 | 248.0 |
| 35 | 25 | 290.0 |

EXAMPLES 36–40 ARE OTHER DIAMINES WHERE d IS 1 AND e IS ZERO

EXAMPLE 36

Preparation of Tallowoxyethypropylamine Propylnitrile (Cyanoethylation of Ether Mono Amine)

To a suitable reaction flask is added 349 grams of tallowoxyethylpropylamine (example 26). Heat while under agitation to 40° C. A nitrogen blanket is applied to the headspace of the reaction vessel. Keep the reaction flask headspace blanketed with nitrogen throughout the entire reaction period. Begin addition of 60 grams of acrylonitrile under good agitation keeping the temperature below 50° C. When all of the acrylonitrile has been added, let react for two hours at 50° C.

Preparation of Diamine (Hydrogenation)

Charge the etheramine propylnitrile as prepared to an autoclave that is capable of operating at pressures up to 600 psig. Carefully charge known quantity of metal catalyst such as Raney® Nickel to the vessel. Use 2% by weight of the total batch. Seal autoclave and start agitation, increase heat to about 80 to 100° C. and vacuum strip out any water that may have been introduced during cyanoethylation or from the Raney® Nickel. When no more water appears on the condenser of the vacuum setup, close autoclave and charge hydrogen gas to about 5 psig. Charge ammonia to vessel up to about 60–70 psig. Increase heat to 135° C. and not pressure. Add hydrogen such that about 150–200 psig. Additional pressure is measured on the autoclave pressure gauge. Maintain this increase with hydrogen gas that will be rapidly taken up by the reaction mixture during the first hour of the reaction. Maintain continuous hydrogen addition in this manner for a period of 4–6 hours. After this time, close the valve from the hydrogen to the autoclave and note pressure on pressure gauge. If pressure is stable and does not decrease after 15 minutes, reaction is complete. Otherwise, continue adding hydrogen as previously described for one hour and then re-check.

Example 36 is repeated, only this time replacing the etheramine of example 36 with the type and quantity of monoetheramine shown below.

| Etherdiamine (e is 0) | Ethermonoamine | |
|---|---|---|
| Example | Example | Grams |
| 37 | 27 | 408 |
| 38 | 28 | 1,596 |
| 39 | 29 | 2,144 |
| 40 | 30 | 2,450 |

The above ether diamines (Examples 31–40) of this invention are used to prepare tertiary amines and their derivatives.

Compounds of the Present Invention

The introduction of the ether group into the molecule together with the specific ethyl branching introduced by using 2-pentenenitrile result in a product having superior liquidity. Liquidity is a property desirable in many applications. There are not many options available to improve liquidity. The material with the highest melting point in a series is the fully saturated product. One way to improve liquidity is to introduce unsaturation. This is why oleyl products with one double bond are much more liquid than stearyl products that have the same number of carbon atoms but no double bonds. The difficulty here is that double bonds are susceptible to a process known as rancidity. This process breaks the double bond and forms aldehydic components that are not only reactive with each other, but also have bad odor. The instability limits the utility of unsaturated materials in many applications. We have found that improved liquidity is achieved by introduction of the ether group and the branching found in the 2-pentenenitrile. Standard ether amines and ether diamines that are made with acrylonitrile result in linear materials that do not have the same degree of improved liquidity as the ether amines and ether diamines that are derived from using 2-pentenenitrile in place of acrylonitrile.

Additionally, the products can be formulated at higher % actives. The introduction of the branching allows for improved solvency, and ease of formulation for use as corrosion inhibitors, biocides, asphalt emulsifiers, fuel additives, herbicide and pesticide surfactants and adjutants.

EXAMPLES 41–50

| Alkoxylated Tertiary Diamine | Ether Diamine Compound | | Ethylene Oxide | Propylene Oxide |
|---|---|---|---|---|
| Example | Example | Grams | Grams | Grams |
| 41 | 31 | 361.0 | 220.0 | 0.0 |
| 42 | 32 | 525.0 | 0.0 | 116.0 |
| 43 | 33 | 305.0 | 88.0 | 00 |
| 44 | 34 | 329.0 | 2,640.0 | 0.0 |
| 45 | 35 | 375.0 | 0.0 | 116.0 |
| 46 | 36 | 406.0 | 88.0 | 0.0 |
| 47 | 37 | 465.0 | 0.0 | 1,160.0 |
| 48 | 38 | 1,653.0 | 440.0 | 580.0 |
| 49 | 39 | 2,201.0 | 44.0 | 116.0 |
| 50 | 40 | 2,507.0 | 0.0 | 116.0 |

The tertiary amine compounds so prepared are referred to herein as alkoxylated tertiary ether diamines and conform to the following structure:

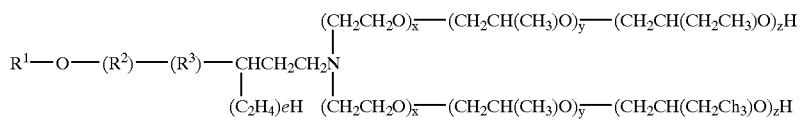

Preparation of Tertiary Amines [Ether Diamine (d=1)]

1. Preparation of Alkoxylated Tertiary Ether Diamine

General Procedure

Step 1.

The specified amount (1 mole) of the ether diamine (Examples 31–40) is charged into an appropriately sized autoclave. The reactor is purged with nitrogen. Alkylene oxide is then reacted at 130–140° C. Approximately 2 hours is required for addition of the alkylene oxide. The reaction mixture is held at 130–140° C. for 2 hours, with stirring. Cool to 70° C. then vent for 10 minutes. Then vacuum strip at 15 to 28 inches of mercury for 30 minutes. The product is low mole alkoxylated diamine.

Step 2.

To the product from the first step was added 0.2 to 0.5% by weight of 45% potassium hydroxide (based upon the total batch weight). By using both vacuum and nitrogen stripping the water level was brought down to below 0.1% by weight. The autoclave was then closed and heated to 110 to 115° C. The specified amount of alkylene oxide (ethylene oxide, propylene oxide, butylene oxide, or combinations thereof) is then added at a rate of one mole per hour. Once all the alkylene oxide has been added the batch is held at constant temperature for two hours. The product is cooled down to 70° C. and vacuum strip at 15 to 28 inches of mercury for thirty minutes. The product is then filtered. The product is the alkoxylated diamine with the required number of moles of alkylene oxide.

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-CH_2CH(CH_2CH_3)O)_c-$;

a, b and c are independently integers ranging from 0 to 30, with the provision that a+b+c are a minimum of 0 and a maximum of 60;

$R^3$ is

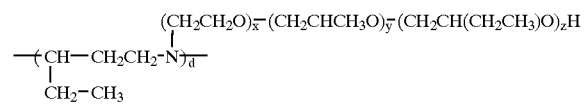

d is 1;

e is 0 or 1;

x, y and z are integers each ranging from 0 to 30 with the provision that x+y+z is a minimum of 2 and a maximum of 60.

1. Preparation of Trimethyl Ether Diamine

General Procedure

In a suitably sized autoclave is charged (1 mole) of the specified diamine (examples 31–40) and 0.5% by weight (based upon the weight of the diamine) of a nickel catalyst G-49-B. Next add 0.5% by weight (based upon the weight of the diamine) of filter aid. Next ad 0.5% by weight (based upon the weight of the formalin) of $NaH_2PO_4$. The contents of the autoclave are then heated to 150° C. Hydrogen is then applied to a pressure of 100 psig, with continuous hydrogen flow and continuous hydrogen venting. Next, 3.1 moles of formaldehyde (96.0 grams) is added as Formalin (37% formaldehyde) at a rate of 0.85 ml per minute. After the addition is complete, the batch is held for 30 minutes. The reaction mass is cooled to 80° C. and vented to atmospheric pressure. The product is the filtered as it is discharged from the autoclave. The product is the desired trimethyl tertiary ether diamine.

EXAMPLE 51–60

| Trimethyl Tertiary Ether Diamine | Ether Diamine Compound | |
|---|---|---|
| Example | Example | Grams |
| 51 | 31 | 360.0 |
| 52 | 32 | 525.0 |
| 53 | 33 | 305.0 |
| 54 | 34 | 329.0 |
| 55 | 35 | 375.0 |
| 56 | 36 | 408.0 |
| 57 | 37 | 465.0 |
| 58 | 38 | 1,653.0 |
| 59 | 39 | 2,201.0 |
| 60 | 40 | 2,507.0 |

The tertiary amine compounds so prepared are referred to herein as methylated tertiary ether diamines and conform to the following structure:

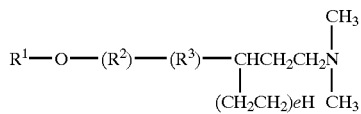

$R^1$ is selected from the group consisting of alkyl having 3 to 22 carbon atoms, aryl having 6 to 20 carbon atoms;

$R^2$ is $-(CH_2CH_2O)_a-(CH_2CH(CH_3)O)_b-(CH_2CH(CH_2CH_3)O)_c-$;

a, b and c are independently integers ranging from 0 to 30, with the provision that a+b+c are a minimum of 0 and a maximum of 60;

$R^3$

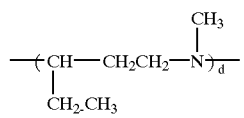

d is 1;
e is 0 or 1.

Preparation of Tertiary Diamine Derivatives

1. Preparation of Methyl Chloride Quaternary Compound

General Procedure

In a stainless Parr autoclave was added one mole of tertiary amine (examples 41, 46, 51, 56) 1% sodium bicarbonate (based upon the weight of the tertiary amine), and isopropanol (based upon the desired activity and viscosity).

The autoclave is sealed, agitation applied and a nitrogen purge applied. The temperature is raised to 85° C. Charge 2.25 moles (114.8 grams) of methyl chloride slowly, so that the temperature is maintained between 80° C. and 90° C. After all the methyl chloride is added, keep the temperature at 80° C. for two hours under agitation. Cool down and filter. The product is used without additional purification.

| Methyl Chloride Quat | Tertiary Diamine | | Isopropanol |
|---|---|---|---|
| Example | Example | Grams | Grams |
| 61 | 41 | 581.0 | 228.0 |
| 66 | 46 | 494.0 | 200.0 |
| 71 | 51 | 402.0 | 168.0 |
| 76 | 56 | 550.0 | 217.0 |

1. Preparation of Methyl Sulfate Quaternary Compound

Procedure

In a 4 necked flask containing a thermometer, mechanical stirrer, condenser and dropping funnel was added 1 mole of tertiary amine (examples 42, 47, 52, 57) and isopropanol (based upon the desired activity of the final quaternary compound) and 3% water (based upon the tertiary amine weight). The contents were heated with stirring to 70° C. while adding 2.17 moles of dimethylsulfate (283.5 grams) from the dropping funnel over 1 hour. The mixture was stirred at 70° C. for 1 our after the addition was complete. The desired pentylammonium methylsulfate compound was cooled and filtered.

| Methyl Sulfate Quat | Tertiary Diamine | | Isopropanol |
|---|---|---|---|
| Example | Example | Grams | Grams |
| 62 | 42 | 641.0 | 298.0 |
| 67 | 47 | 1,625.0 | 626.0 |
| 72 | 52 | 567.0 | 278.0 |
| 77 | 57 | 507.0 | 253.0 |

1. Preparation of Amine Oxide

Procedure

In a four necked flask equipped with a stirrer, dropping funnel, and a thermometer, is added 1.0 mole of the specified tertiary amine (examples 44, 49, 54, 59). Next is added isopropanol to make the desired activity and viscosity of the amine oxide. The mixture was stirred and slowly heated. 229.5 grams of 35% hydrogen peroxide (2.37 moles of $H_2O_2$) is added dropwise keeping the temperature between 55° C. and 65° C. The rate of addition is determined by the exotherm, keeping the temperature of the reaction in the specified range. After the addition, the reaction was held to 60° C.–65° C. for 2 hours. The amine oxide is obtained and utilized without purification.

| Amine Oxide | Tertiary Diamine | | Isopropanol |
|---|---|---|---|
| Example | Example | Grams | Grams |
| 64 | 44 | 2,961.0 | 2,847.0 |
| 69 | 49 | 2,361.0 | 2,242.0 |
| 74 | 54 | 371.0 | 253.0 |
| 79 | 59 | 2,243.0 | 2,125.0 |

1. Preparation of Benzyl Chloride Quaternary Compound

General Procedure

In a four neck flask equipped with a thermometer, condenser, dropping funnel and mechanical stirred was added one mole of tertiary amine (examples 43, 48, 53, 58). Next add, 1% by weight of sodium bicarbonate (based upon the weight of the tertiary amine), 3% by weight (based upon the weight of the tertiary amine), and isopropanol (based upon the desired activity and viscosity of the final quaternary compound). Stir and heat to 80° C.–85° C., under a nitrogen blanket. Add 2.25 moles of benzyl chloride (285.8 grams), while maintaining the temperature in the range of 80° C.–85° C. After the addition is complete, hold the contents at 80° C.–85° C. for two hours. Cool the contents and filter. The product is used without additional purification.

| Benzyl Chloride Quat | Tertiary Diamine | | Isopropanol |
|---|---|---|---|
| Example | Example | Grams | Grams |
| 63 | 43 | 393.0 | 216.0 |
| 68 | 48 | 2,673.0 | 976.0 |
| 73 | 53 | 347.0 | 201.0 |
| 78 | 58 | 1,695.0 | 650.0 |

The compounds of the present invention are outstanding surface active agents, providing outstanding emulsification, detergency and foaming properties. By the proper selection the surfactants of the present invention can be oil, or water soluble, and be used to make oil in water, or water in oil emulsions. The branching gives better liquidity, making the compounds useful in cold emulsification processes. In addition the compounds of the present invention emulsify greater quantities of oil than do conventional surfactants.

What is claimed:

1. An ether diamine quaternary conforming to the following structure:

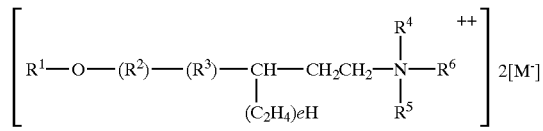

wherein:

$R^1$ is selected from the group consisting of alkyl having 3 to 22 carbon atoms, $R^2$ is $-(CH_2CH_2O)_a-(CH_2CH(CH_3)O)_b-(CH_2CH(CH_2CH_3)O)_c-$;

a, b and c are independent integers ranging from 0 to 30;

$R^3$ is

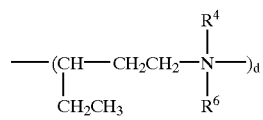

d is 1;

e is 0 or 1;

$R^4$ and $R^5$ are selected from the group consisting of $-CH_3$; and $-CH_2CH_2O)_x-(CH_2CH(CH_3)O)_y-(CH_2CH(CH_2CH_3)O)_zH$;

x, y and z are independent integers ranging from 0 to 20, with the provision that x+y+z is greater than or equal to 3;

$R^6$ is selected from the group consisting of $-CH_3$ and $-CH_2-C_6H_6$;

M is an appropriate anion needed for charge balance and is selected from the group consisting of Cl, Br, and $CH_3SO_4$.

2. An ether diamine quaternary of claim 1 wherein $R^1$ is $C_3H_7$, b is 5, $R^4$, $R^5$ and $R^6$ are $CH_3$ and M is $CH_3SO_4$, and e is 1.

* * * * *